United States Patent [19]

Yamaguchi

[11] Patent Number: 4,822,445

[45] Date of Patent: Apr. 18, 1989

[54] APPARATUS FOR PROCESSING DOUBLE FACE ADHESIVE TAPE

[75] Inventor: Akira Yamaguchi, Saitama, Japan

[73] Assignee: Fuji Photo Film Co., Ltd., Kanagawa, Japan

[21] Appl. No.: 118,721

[22] Filed: Nov. 9, 1987

[30] Foreign Application Priority Data

Nov. 21, 1986 [JP] Japan ................................. 61-276671
Nov. 21, 1986 [JP] Japan ................................. 61-276672
Mar. 11, 1987 [JP] Japan ................................. 62-54195

[51] Int. Cl.⁴ ............................................. B32B 31/18
[52] U.S. Cl. ..................................... 156/510; 156/252; 156/268; 156/271; 156/344; 156/513; 156/514; 156/522; 156/584; 204/416; 204/417; 204/418
[58] Field of Search ............... 156/252, 253, 245, 268, 156/269, 270, 271, 289, 313, 344, 259, 513, 514, 522, 584, 510; 204/416, 417, 418, 419

[56] References Cited

U.S. PATENT DOCUMENTS

| | | | |
|---|---|---|---|
| 2,303,346 | 12/1942 | Flood | 156/269 |
| 4,336,091 | 6/1982 | Gottermeier | 156/259 |
| 4,393,584 | 7/1983 | Bare et al. | 29/877 |
| 4,599,125 | 7/1986 | Buck | 156/513 |
| 4,683,048 | 7/1987 | Yamada et al. | 204/416 |
| 4,713,165 | 12/1987 | Conover et al. | 204/418 |

FOREIGN PATENT DOCUMENTS

2722617 12/1977 Fed. Rep. of Germany.
58-211648 12/1983 Japan.
629264 1/1987 Japan.

*Primary Examiner*—Caleb Weston
*Attorney, Agent, or Firm*—Jules E. Goldberg

[57] ABSTRACT

An apparatus for processing a double face adhesive tape so as to attach at least one member thereto, comprising a roll of the double face adhesive tape having release papers attached to both faces, a drawing out means of the double face adhesive tape from said roll, a slitting means to slit at least the vicinity of one side edge of the upper release paper or the lower release paper of the double face adhesive tape parallel to said side edge, a separating means to separate the slit release paper leaving at least one side portion of the slit release paper attached, and an attaching means to attach at least one member on the exposed face of the double face adhesive tape is disclosed. The drawing out means intermittently draws out the double face adhesive tape from the roll, and a punching means to punch the double face adhesive tape to form hole(s) is further incorporated. Also provided are a cutting means to cut the remaining release paper and the double face adhesive tape to a size smaller than the attached face of said member and a detaching means to detach the member and the cut release paper and the cut double face adhesive tape from the double face adhesive tape.

6 Claims, 7 Drawing Sheets

APPARATUS FOR PROCESSING DOUBLE FACE ADHESIVE TAPE

BACKGROUND OF THE INVENTION

Field of the Invention

This invention relates to an apparatus for processing a double face adhesive tape by releasing its release paper and attaching at least one member to it. More particularly, this invention relates to an apparatus for processing a double face adhesive tape suitable for the process assembling an instrument for dry analysis for measuring concentration or activity of a particular component in a liquid sample, such as a device for measuring ionic activity.

Description of the Prior Art

Recently, ionic activity-measuring instruments utilizing an ion selective electrode, particularly dry-type ionic activity-measuring devices utilizing planar ion selective electrodes, have been developed because they can rapidly, simply and accurately measure ionic activity of a liquid sample. Examples of the dry-type ionic activity-measuring device are disclosed in German Patent No. 2,722,617.

Figure 14:
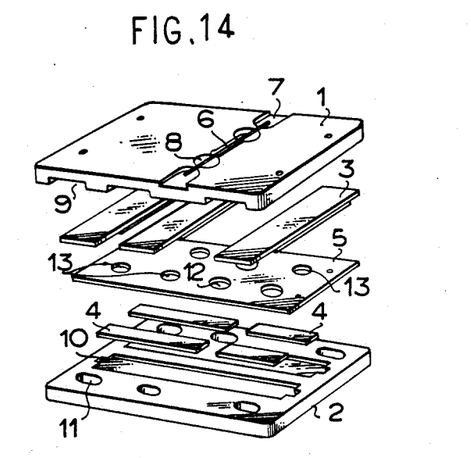
FIG. 14 is an exploded perspective view of the ionic activity-measuring device.

As the modification, a dry-type ionic activity-measuring device capable of measuring ionic activity of two or more kinds of ions at the same time has also been developed (Japanese Patent KOKAI No. 58-211648 and Japanese Patent Application No. 60-148564). The dry-type multiple ionic activity-measuring device disclosed in the specification of Japanese Patent Application No. 60-148564 is composed of an upper frame 1, a lower frame 2, planar electrodes 3, liquid-distributing members 4 and a double face adhesive tape 5 as shown in FIG. 14. A bridge groove 7 for a bridge 6 and two spotting holes 8 are provided in the upper frame 1. Sample liquid is spotted in one of the holes 8, and reference solution is spotted in the other hole 8. Three shallow channels 9 for placing the planar electrode 3 are formed on the lower surface of the upper frame 1. A pair of shallow rectangular concavities 10 are formed in parallel on the upper surface of the lower frame 2, and terminal holes 11 for connecting a leading wire to the electrodes 3 are provided on both side portions of the lower frame 2. Two pairs of the liquid-distributing members 4 are placed in the concavities 10. The double face adhesive tape 5 is punched to form a pair of spotting holes 12 and three pairs of liquid supply holes 13. The sample liquid and the reference solution spotted into the spotting holes 8 pass through the respective liquid-distributing member 4, and are supplied to each electrode 3 through the liquid supply hole 13.

Such a dry-type multiple ionic activity-measuring device is assembled by punching the double face adhesive tape 5 to form the holes 12, 13, attaching the upper frame 1 and the electrodes 3 to the upper face of the double face adhesive tape 5 and attaching the lower frame 2 and the liquid-distributing members 4 to the lower face of the double face adhesive tape 5. Generally speaking, the release papers are preferably left on the double face adhesive tape up to immediately before the attachment of the object member in order to avoid undesirable attachment. Moreover, it is not so easy to convey smoothly the double face adhesive tape of which the release papers have been removed on use, and accordingly, a particular means is necessary. Besides, after the necessary attachment is finished, useless part of the double face adhesive tape must be removed.

In addition, when the double face adhesive tape is projected from the edge of the upper frame or the lower frame attached thereto after removing the useless part, trouble by undesirable adhesion occurs at the processing apparatus or with other members in the later processes.

SUMMARY OF THE INVENTION

An object of the invention is to provide a means free from the above problems arising in the process to attach the lower frame and the liquid-distributing member to one side of the double face adhesive tape in order to assemble the ionic activity-measuring device having the above structure, and which carries out this process efficiently.

Another object of the invention is to provide a means free form the above problems arising in the process removing the useless part of the double face adhesive tape and in the processes after that.

Another object of the invention is to provide a means free from the above problems arising in the process to attach at least one member to one side of a double face adhesive tape in order to assemble two or more members by attaching to the double face adhesive tape into an article, not limited to the ionic activity-measuring device, and which carries out this process efficiently.

The present invention has been made in order to achieve the above objects, and provides an apparatus for processing a double face adhesive tape to which at least one member is attached, characterized by the drawing out means to draw out the double face adhesive tape where at least one side portion of the double face adhesive tape is left and the double face adhesive tape is pulled by utilizing the remaining portion of release paper, the punching means of the double face adhesive tape where the double face adhesive tape is intermittently drawn out and it is punched during stopping, the cutting means to cut the double face adhesive tape having a member attached to one face and a release paper on the other in size smaller than the attaching face of the member so as not to protrude from the member, and the means for detaching the above member leaving the cut double face adhesive tape attached thereto.

DETAILED DESCRIPTION OF THE INVENTION

Figure 1:
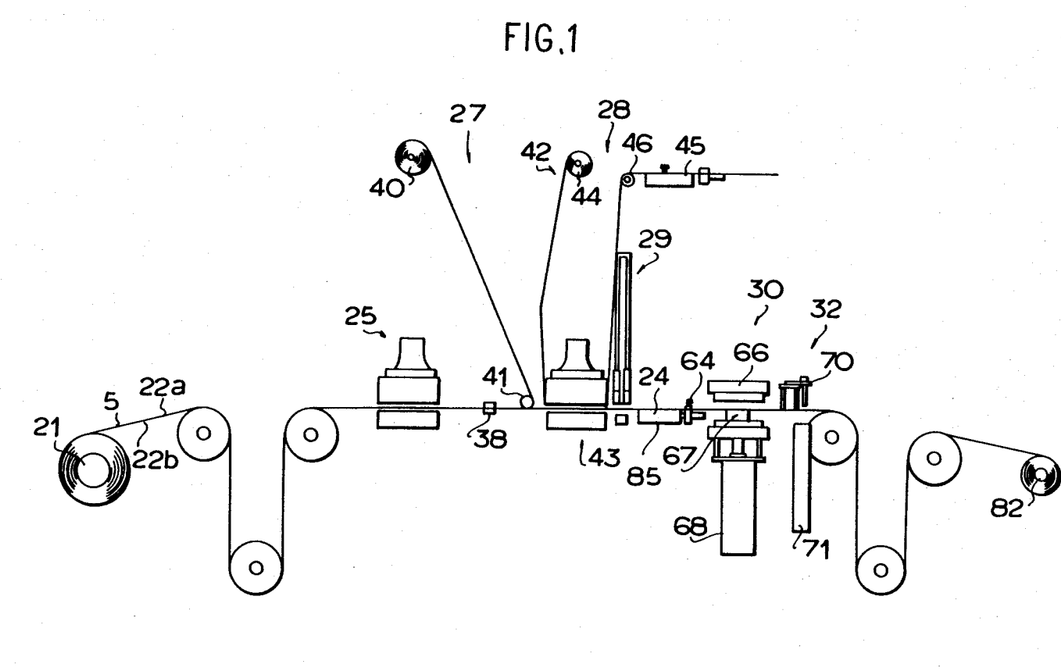
FIG. 1 is a schematic diagram of an apparatus embodying the invention.

The double face adhesive tape is coiled around a roll, and two release papers are attached to cover both faces of the adhesive tape. The adhesive tape is intermittently drawn out from the roll by the drawing out means by prescribed lengths, and a slit or two is given to the vicinity of one side edge of the upper release paper or the lower release paper of the double face adhesive tape in the longitudinal direction of the tape. The slitting means may involve cutting by press using a knife or cutting by a rotating knife. The slitting means corresponds to the knife 35 of the punching and slitting means 25 shown in FIG. 8. The punching means punches the double face adhesive tape to form necessary holes through it. The type of slitting means may be determined according to the size, shape or number of the holes, and therefore they may be of two or more kinds. In the case of the ionic activity-measuring device shown in FIG. 13, the holes includes the spotting holes 12 and liquid supply holes 13, and the punching means corresponds to the punches 34 shown in FIG. 8. The separating means is the means to separate the slit release paper, leaving at least one side portion of the slit release paper attached to the double face adhesive tape in the vicinity of the edge. This separating means corresponds to the rolls 40, 41 shown in FIG. 1. The release paper remaining at the side portion is utilized for conveying the tape. The attaching means is the means to attach at least one member on the exposed adhesive face of the double face adhesive tape exposed after separation of the slit release paper described above. Two or more attaching means may be utilzied so as to attach two or more members. In the case of the ionic activity-measuring device shown in FIG. 14, the members to be attached include the liquid-distributing members 4, the lower frame 2, the sheet electrodes 3 and the upper frame 1. The attaching means in the apparatus of FIG. 1 is the liquid-distributing member attaching means 28 and the lower frame-attaching means 29. The cutting means is the means to cut the double face adhesive tape and the lower release paper in a size being smaller than the attaching face of the member, as they are attached to it. The size is preferably smaller the attaching face by about 0.1 to 1 mm. The cut double face adhesive face may not be similar to the attaching face. This cutting means corresponds to the cutting means 30 shown in FIG. 1. The detaching means in the means to detach the member attached to the double face adhesive tape carrying the cut double face adhesive tape with the cut lower release paper from the rest of the tape. This means may involve process such as suction or pushing out. The roll, the slitting means, the separating means, the attaching means, the cutting means and the detaching means are provided in this order. While, the drawing out means may be disposed between any of the above means or behind the attachment means. However, it is preferred to dispose it between the roll and the slitting means or behind the attaching means.

An embodiment of the invention is illustrated in FIG. 1.

Figure 2:
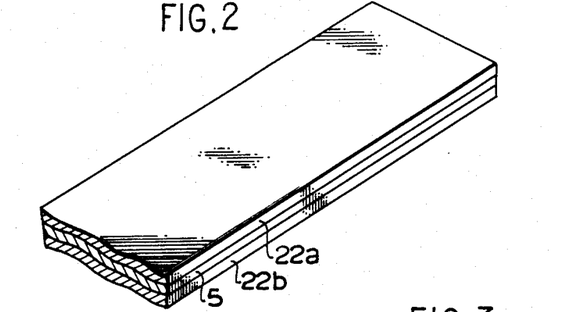
FIGS. 2 to 7 are perspective views indicating the processed states of the double face adhesive tape at several positions of the apparatus of FIG. 1.

A double face adhesive tape 5 is coiled around a roll 21. As shown in FIG. 2, upper release paper 22a and lower release paper 22b are attached to cover both faces of the adhesive tape 5. As shown in FIG. 1, the double face adhesive tape 5 is drawn out of the roll 21, and passed through a punching and slitting means 25, positioning rollers 38, a separating means 27, a liquid-distributing member-attaching means 28, a lower frame-attaching means 29, a drawing out means 24, a cutting means 30 of the lower release paper 22b and the double face adhesive tape 5 and a detracting means 32 of partially assembled ionic activity-measuring device, successively. Thereafter, remaining double face adhesive tape is coiled again around a roll 82.

Figure 3:
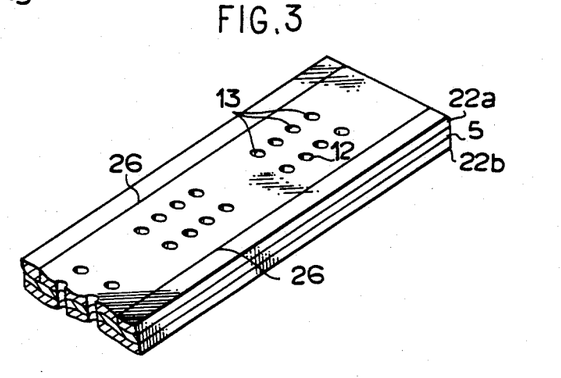
Figure 8:
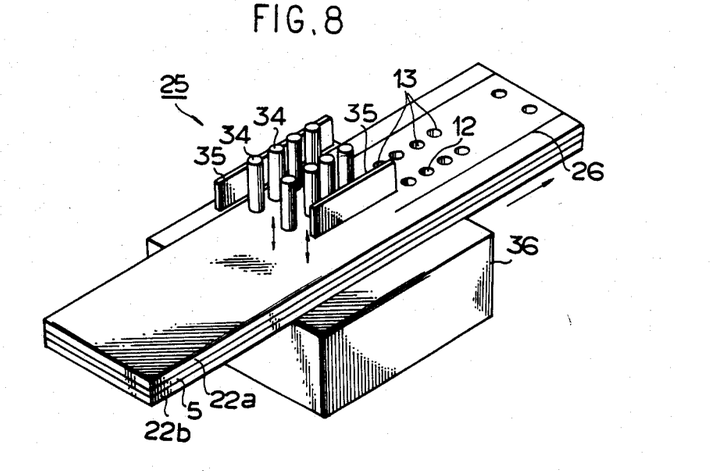
FIG. 8 is a perspective view which indicates punching and slitting stage of the double face adhesive tape.

The punching and slitting means 25 comprises, as shown in FIG. 8, eight punches 34 arranged in two rows, a pair of knives 35 and die 36, knives 35 being dispoesd on the outside of the punches 34. Eight punch holes (not illustrated in the drawings) are provided on the upper face of the die 36 at the positions corresponding to the punches 34. The punches 34 and the knives 35 descend simultaneously, and cut the double adhesive tape 5. On that occasion, the punches 34 punch the upper release paper 22a, the double face adhesive tape 5 and the lower release paper 22b to form two spotting holes 12 and six liquid supply holes 13. While, the knives 35 cut only the upper release paper 22a parallel to the side edge of the double face adhesive tape 5. The length of each knife 35 is the same as or slightly longer than single moving length of the double face adhesive tape which moves intermittently, and the cut lines formed by respective motions are joined to form two continuous slits 26 near both side edges of the double adhesive tape 5. The state of the double face adhesive tape treated by punching and slitting means is shown in FIG. 3.

Figure 9:
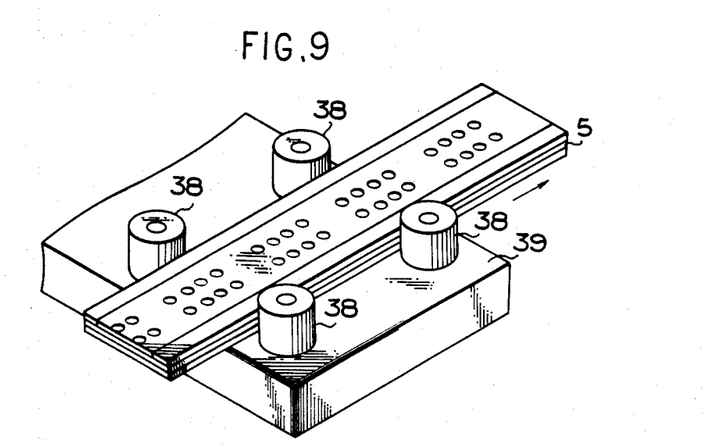
FIG. 9 is a perspective view indicating positioning rollers.

The positioning rollers 38 are provided between the punching and slitting means 25 and separating means 25. As shown in FIG. 9, two pairs of position rollers 38 are rotatably mounted on the base 39 at almost the same distance as the width of the double face adhesive tape 5. These positioning rollers 38 are provided in order that the liquid-distributing members 4 and the lower frame 2 are attached at accurate positions at their attaching means 28, 29. The double face adhesive tape is not braked nor deflected during its movement by the positioning rollers 38, even though paste is exposed at edges of the adhesive tape.

Figure 4:
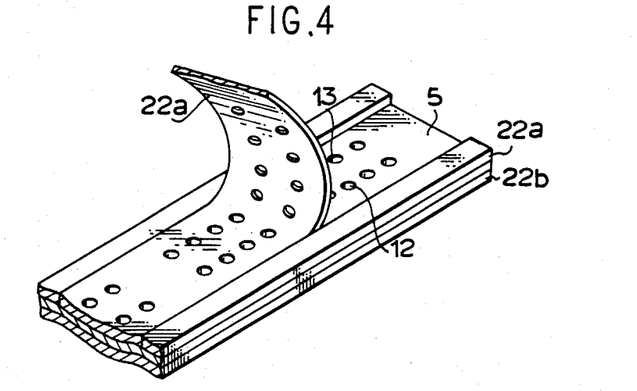

The separating means 27 separates the central part of the upper release paper 22a leaving both side portions attached to the adhesive tape 5 as shown in FIG. 4. This means 27 is, as shown in FIG. 1, constituted by a stripping roll 41 to strip the central part of the upper release paper 22a and a take-up roll 40 to wind it.

Figure 5:
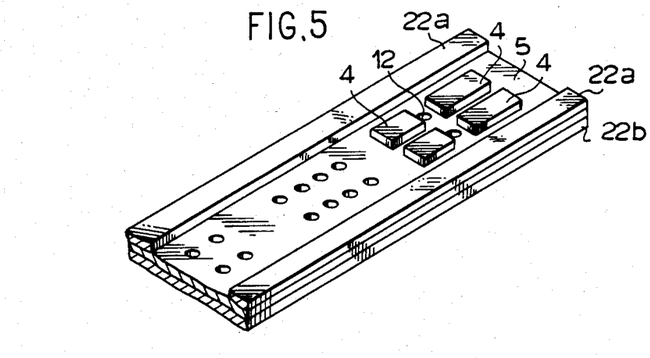
Figure 10:
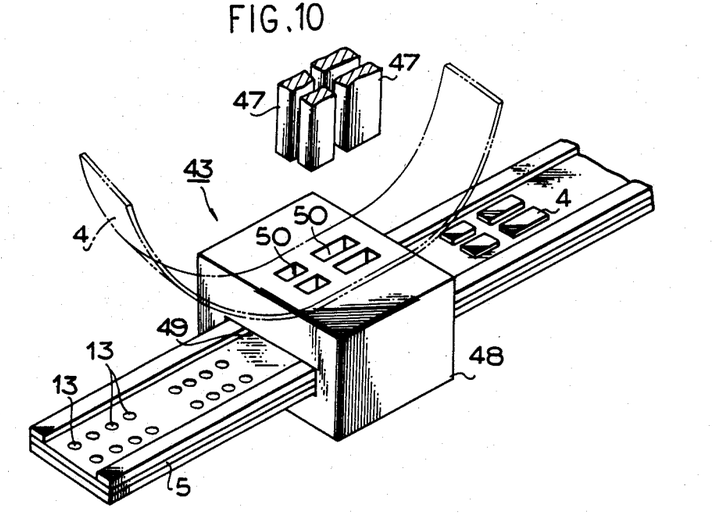
FIG. 10 is a perspective view which indicates supplying and attaching stage of liquid-distributing members to the double face adhesive tape.

The liquid-distributing member-attaching means 28 is the means to attach the liquid-distributing members 4 to the double face adhesive tape 5. This means 28 is, as shown in FIG. 1, constituted by a liquid-distributing member supply part 42 and a punching and attaching part 43. The liquid-distributing member supply part 42 supplies the liquid-distributing member in the form of a tape to the punching and attaching part 43, and it is constituted by a supply roll 44, an air feeder 45 and an intermediate roll 46. The tape of the liquid-distributing member is coiled around the supply roll 44, and it is intermittently drawn out by the air feeder 45 by prescribed lengths. The air feeder is constituted by an air cylinder and a grasping mechanism to grasp the tape of the liquid-distributing member. The punching and attaching part 43 is, as shown in FIG. 10, constituted by a punch 47 and a die 48. The die 48 is provided with a guide tunnel 49 for passing the double face adhesive tape 5 to penetrate the die 48 in a horizontal direction and four punch holes 50 for the insertion of the punches 47 to reach the guide tunnel 49 in a vertical direction. The tape of the liquid-distributing member 4 travels on the upper face of the die 48, and punched by the punches 47 so as to be attached by the punches 47 to the double face adhesive tape 5 and to cover the liquid supply holes 13. FIG. 5 indicates the state of the double face adhesive tape 5 at the place of the liquid-distributing member-attaching means. As shown in FIG. 5, the punched liquid-distributing members 4 are composed of four pieces, a pairs of short pieces and a pair of long pieces. The short piece covers liquid supply hole 13 located on the left side in FIG. 5, and the long piece covers two liquid supply holes 13 in the longitudinal direction of the double face adhesive tape 5.

Figure 6:
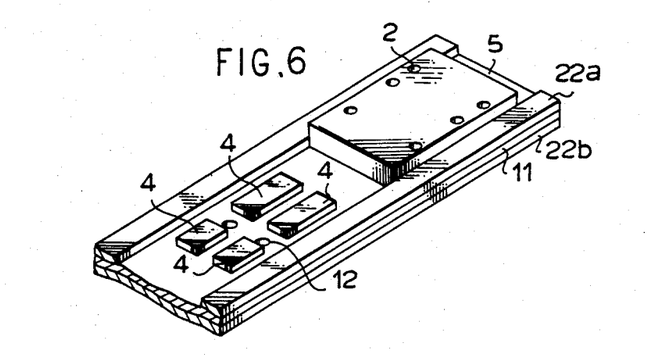
Figure 11:
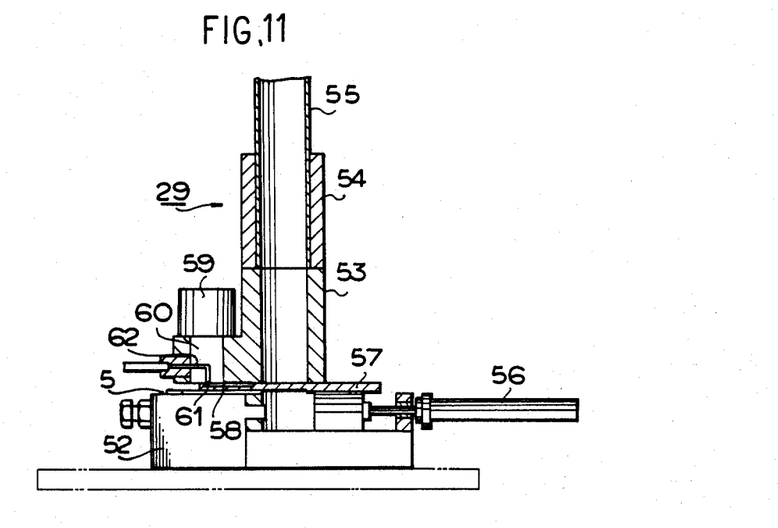
FIG. 11 is a side view, partly in cross section, of the attaching means of the lower frame.

The lower frame-attaching means 29 is the means to attach the lower frame 2 to the double face adhesive tape 5 on which the liquid-distributing members 4 have been attached. FIG. 11 is a side view, partly in cross section, of this attaching means 29 looked from the travelling direction of the double face adhesive tape 5. This means 29 is, as shown in FIG. 11, constituted by a base 52, a guide 53, a holder 54, a magazine 55, a cylinder 56, a slider 57, another cylinder 59 and a suction block 60. The double face adhesive tape 5 travels on the upper face of the base 52. The magazine 55 is the storage place of the lower frames 2, and fitted in the holder 54. The guide is an intermediate member to guide the lower frames 5 stacked in the magazine 55 to the slider 57. The slider 57 is disposed under the guide 53, and it is moved forward and backward by the cylinder 56. A concavity 58 to receive one piece of the lower frame 2 is formed on the upper face of the slider 57. A suction hole 62 is bored in the suction block 60 to the underside to form a suction opening 61. A suction means such as a suction pump (not illustrated) is connected to the suction hole 62. The suction block 60 is moved by the cylinder 59 in a vertical direction. The lower frames 2 are stacked in the magazine 55 and the guide 53 and supplied one by one to the underside of the suction block 60. Each lower frame is held by the suction, and attached to the double face adhesive tape by descending the suction block 60. FIG. 6 indicates the state of the double face adhesive tape 5 placed at the lower frame-attaching means. The lower frame 2 is attached to the double face adhesive tape 5 so as to fit the liquid-distributing members 4 to the concavities 10 (illustrated in FIG. 14) of the lower frame 2.

The drawing out means 24 is, as shown in FIG. 1, constituted by an air cylinder 85 and a grasp part 64 joined to the shaft of the air cylinder 85. The grasp part 64 grasps both side edges where the upper release paper 22a remains, and the double face adhesive tape 5 is intermittently drawn out of the roll 21.

Figure 7:
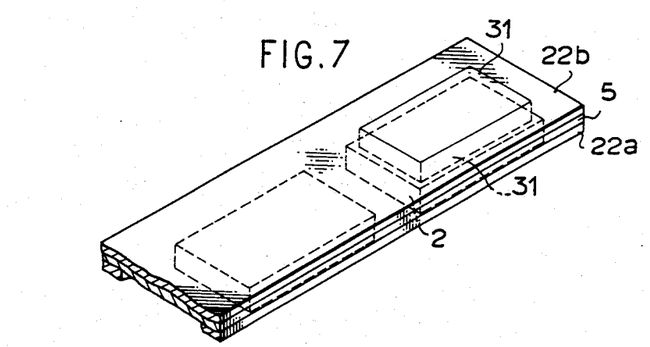

The cutting means 30 cuts the lower release paper 22b and the double face adhesive tape 5 in the square slightly smaller than the lower frame 2 as shown in FIG. 7. In the drawing, 31 indicates the cut line. By this size, all terminal holes 11, shown in FIG. 14, are exposed out of the double face adhesive tape 5 so as to connect lead wires to the planar electrodes 3. As shown in FIG. 1, the cutting means 30 is constituted by an upper die 66, a lower die 67 and a cylinder 68 which moves the lower die 67 in a vertical direction to cut the lower release paper and the double face adhesive tape by pressing.

Figure 12:
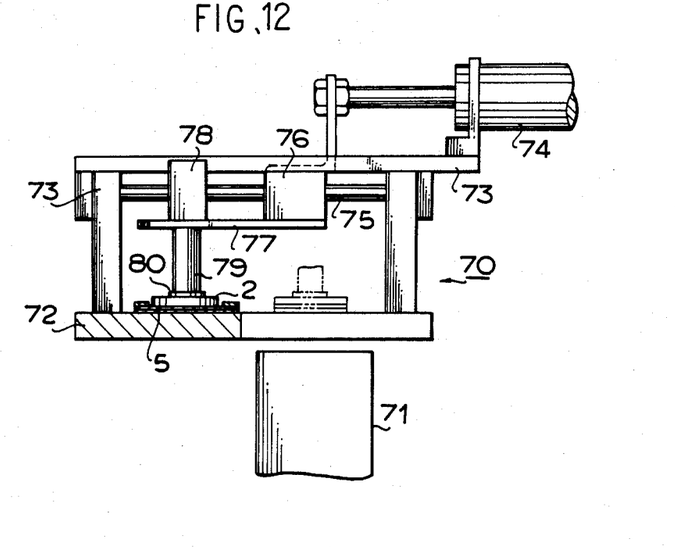
FIG. 12 is a side view, partly in cross section, of the detaching means associated with the partially assembled ionic activity-measuring device.

The detaching means 32 is the means to separate the partially assembled ionic activity-measuring device assembled in the foregoing processes along the cut line 31 of FIG. 7, and to detach it from the traveling double face adhesive tape 5. The detaching means 32 is constituted by a lower frame suction part 70 and a discharge magazine 71. As shown in FIG. 12, the lower frame suction part 70 is mainly constituted by a base 72, a suction member 79 to suck the lower frame 2 and two air cylinders 74, 78 which moves the suction member vertically and horizontally, respectively. The double face adhesive tape 5 travels on the upper face of the base 72. A frame 73 is attached to the base 72, and the air cylinder 74 is mounted on an upper edge of the frame 73. The other air cylinder 78 and the suction member 79 are fixed on the end of the shaft of the air cylinder 74 through a carrier bar 77 and a slide member 76 sliding on a slide bar 75. The opening 80 of the suction member 79 sucks the lower frame 2 attached on the double face adhesive tape 5. The partially assembled product is detached from the travelling tape 5 by elevating the suction member 79 by the action of the air cylinder 7, and then carried to the position above the discharge magazine 71 by the action of the air cylinder 74, and put into the discharge magazine 71 by deactivating the air cylinder 78.

Figure 13:
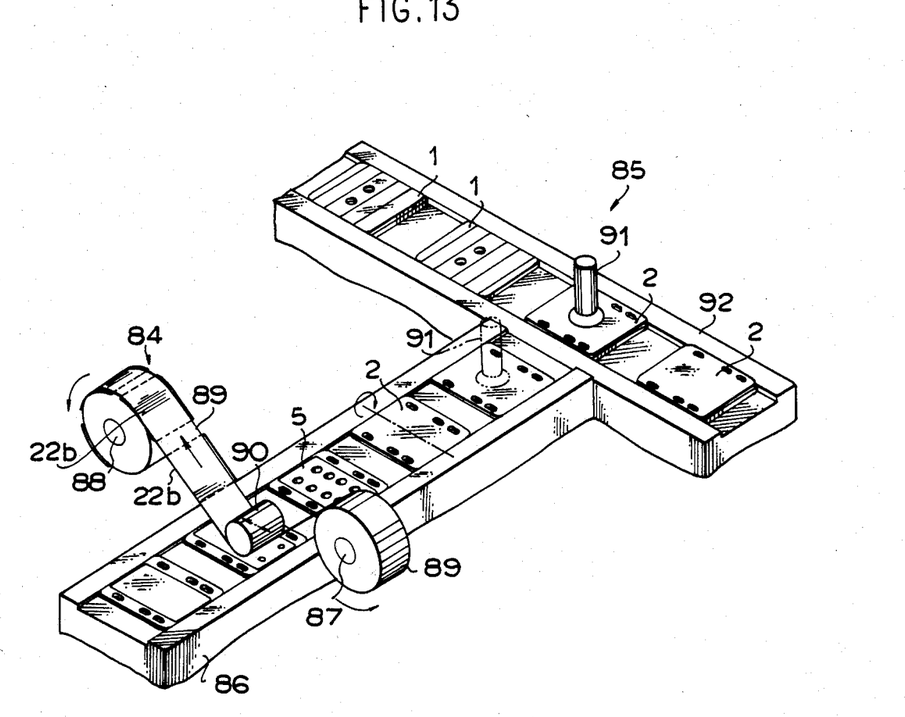
FIG. 13 is a perspective view which indicates the separating stage of lower release paper and attaching stage of upper frame to which planar electrodes have been attached.

The recovered partially assembled products are sent to the next process, and the remaining members are further assembled. FIG. 13 shows the state of the lower release paper 22b being separated from the double face adhesive tape attached to the lower frame 2 and the state of the upper frame 1 being attached to the double face adhesive tape 5. This apparatus is composed of an intermittent conveying means 86, a separating means 84 to separate the lower release paper 22b, and an attaching means 85 to attach the upper frame 1. The intermittent conveying means 86 intermittently conveys the partially assembled products recovered into the discharge magazine by prescribed lengths. The separating means 85 is composed of a delivery roll 87, a take-up roll 88, a single face adhesive tape 89 wound around the delivery roll 87 and laid across the conveying means 86 to the take-up roll 88, and a pressure roller 90 movable in vertical and horizontal direction and, rollable on the lower release paper 22b of the partially assembled products conveyed by the conveying means 86. The conveying means 86 is provided with a known mechanism for reversing the partially assembled product near its end (not illustrated in the drawing). The attaching means 85 is composed of an upper frame conveyor 92 installed at a right angle to the conveying means 81 and a suction transferring member 91 to transfer the reversed partially assembled product from the end of the conveying means 86 to the upper frame conveyor 92. The upper frame conveyer 92 also intermittently conveys the upper frame 1.

This apparatus is operated as follows:

First, a double face adhesive tape 5 is laid from the roll 21 to the roll 22 through each means. At that time, the slit 26 is not formed yet. The air feeder 24 is started, and the double face adhesive tape 5 is intermittently conveyed by prescribed lengths. At each standing between movements, the punches 34 and the knives 35 descend, and each sets of spotting holes 12 and liquid supply holes 13 penetrating three layers and two slits 26 cut into the upper release paper 22a only are formed as shown in FIGS. 3 and 8. When the front of the slit 26 reaches the stripping roll 41, the central part of the upper release paper 22a between the slits 26 are separated from the double face adhesive tape 5 as shown in FIG. 4. The tip of the upper release paper 22a separated is attached to coil itself around the take-up roll 40. On the other hand, a tape of liquid-distributing member 4 is delivered from the supply roll 44, and laid through the punching and attaching part 43 and the intermediate roll 46 to the air feeder 45. Both sides of the tip of the liquid-distributing member 4 are grasped by the grasping mechanism of the air feeder 45. The air feeder 45 synchronizes with the other air feeder 24, and draws out the tape of the liquid-distributing member 4 by prescribed lengths intermittently. At each standing between movements, the punches 47 descend and punch the liquid-distributing member tape. Then, they further descend and attach the punched pieces to the prescribed positions of the double face adhesive tape 5 by pressing as shown in FIG. 5. Lower frames 2 are stacked in the magazine 55 shown in FIG. 11, and taken out one by one by the slider 57. When the lower frame 2 resting on the slider 57 reaches the underside of the suction block 60, it is sucked to hold by the suction through the suction hole 62. Then, the slider 57 moves backward, and receives a next piece of the lower frame 2. At each standing between the movements of the double face adhesive tape 5, the suction block 60 descends and presses the lower frame 2 to the double face adhesive tape 5. The suction is stopped, and the suction block 60 releases the lower frame 2. Then, the suction block 60 ascends again. At the drawing out means, the grasp part 64 grasps both side portions of the double face adhesive tape 5 where upper release paper 22a remains, and pulls the prescribed length by the air cylinder 85. Then, the grasp part 64 releases the double face adhesive tape 5, and returns to the first place. The drawing out means repeats these motions. When the double face adhesive tape 5 reaches the cutting means 30, the lower die 67 ascends and presses to cut the double face adhesive tape 5 together with the lower release paper 22b into a square as shown in FIG. 7. Subsequently, the double face adhesive tape 5 travels to the detaching means 32. The suction member 79 moves forward by the cylinder 74, and descends by the cylinder 78. When the suction opening 80 touches the lower frame 2 stuck on the double face adhesive tape 5, the suction opening 80 sucks to hold the lower frame 2. Then, the suction member 79 ascends and detaches the partially assembled ionic activity-measuring device composed of the lower frame 2, four pieces of the liquid-distributing members 4 and the square double face adhesive tape 5 to which the lower release paper 22b is attached. The suction member 79 moves backward, and releases to drop the partially assembled device into the discharge magazine 71 by breaking the suction. The remaining double face adhesive tape is coiled again around the roll 82.

The recovered partially assembled devices are intermittently conveyed by the conveying means 86, as shown in FIG. 13. When the partially assembled device reaches just under the single face adhesive tape 89, the pressure roller 90 descends and rolls on the lower release paper 22b attached on the partially assembled device in the cross direction of the conveying means 86 to attach the lower release paper 22b to the single face adhesive tape 89. then, the pressure roller 90 ascends, and unit length of the single face adhesive tape 89 is wound around the take-up roll 88. The partially assembled device from which the lower release paper 22b is removed is further conveyed, and reversed by the reversal mechanism. The conveying means 86 has the mechanism that the adhesive face of the reversed partially assembled device does not touch any member nor any material. When the reversed partially assembled device reaches the end of the conveying means 86, the suction transferring member 91 descends and takes it by suction. Then, the suction transferring member 91 ascends, and transfers the partially assembled device above the upper frame conveyor 92. On the other hand, the planar electrodes 3 are fitted into the channels 9 of the upper frame 1 shown in FIG. 14, and intermittently conveyed by the upper frame conveyor 92. When the upper frame 1 reaches just under the suction transferring member 91, it descends to press the partially assembled device to the upper frame 1. Thereafter, the suction of the suction transferring member 91 is broken, and it ascends to return the first place. The assembled devices thus manufactured are discharged from the upper frame conveyer 92, and the bridge 6 shown in FIG. 14, leading wires and the like are attached to it to complete the ionic activity-measuring device.

In the apparatus for processing double face adhesive tape of the invention, at least a slit release paper remains on one side edge of the double face adhesive tape, so that it can easily be conveyed by utilizing this remaining release paper without trouble. Therefore, a member can efficiently and accurately be adhered on one face of the double face adhesive tape successively. Furthermore, by cutting into the other release paper and the double face adhesive tape to which the member has been attached in size slightly smaller than the attaching face of the member, this partially assembled product can easily be detached from the double face adhesive tape. Since all side edges of the double face adhesive tape are positioned slightly back from the edge of the adhered member, undesired adhesion does not occur to the processing apparatus or other members in the subsequent processes. The apparatus of the invention is particularly effective in the attachment of the lower frame and the upper frame of an ionic activity-measuring device in mass production, and the frames can accurately and efficiently be attached each other by means of double face adhesive tape.

I claim:

1. In an apparatus for processing a double face adhesive tape whereby at least one face of a member is attached thereto, comprising a roll of the double face adhesive tape having release papers attached to both faces, a drawing out means of the double face adhesive tape from said roll, a separating means to separate the release paper from one of said faces of said tape, an attaching means to attach at least one member on the exposed adhesive face of the double face adhesive tape where the release paper has been removed, the improvement which comprises incorporating a cutting means to cut the remaining release paper and the double face adhesive tape in a size being smaller than the attached face of said member and a detaching means to detach the member and the cut release paper and the cut double face adhesive tape from the double face adhesive tape.

2. The apparatus of claim 1 wherein said member is the lower frame of an ionic activity-measuring device, and which further comprises a separating means to separate the remaining release paper and an attaching means to attach a second frame on the exposed adhesive face of the double face adhesive tape where the release paper has been removed.

3. The apparatus of claim 1 wherein said member is an upper frame of an ionic activity-measuring device, and which further comprises a separating means to separate the remaining release paper and an attaching means to attach a lower frame of an ionic activity-measuring device on the exposed adhesive face of the double face adhesive tape where the release paper has been removed.

4. The apparatus of claim 1 which further comprises a slitting means to slit at least the vicinity of one side edge of the release paper from one face of the double face adhesive tape parallel to said side edge, and said separating means is to separate the slit release paper leaving at least one of the side portion of the slit release paper attached to the tape.

5. The apparatus of claim 4 wherein said member is liquid-distributing member(s) and a frame to receive themof an ionic activity-measuring device.

6. The apparatus of claim 4 wherein said member is a frame to receive liquid-distributing member(s) of an ionic activity-measuring device.

* * * * *